United States Patent
Smith et al.

(10) Patent No.: US 11,504,525 B2
(45) Date of Patent: Nov. 22, 2022

(54) METHODS AND APPARATUS FOR A LEAD FIXATION DEVICE

(71) Applicants: Kris A. Smith, Phoenix, AZ (US); Matthew G. Marek, Plano, TX (US)

(72) Inventors: Kris A. Smith, Phoenix, AZ (US); Matthew G. Marek, Plano, TX (US)

(*) Notice: Subject to any disclaimer, the term of this patent is extended or adjusted under 35 U.S.C. 154(b) by 101 days.

(21) Appl. No.: 16/675,448

(22) Filed: Nov. 6, 2019

(65) Prior Publication Data

US 2020/0139110 A1    May 7, 2020
US 2022/0062625 A9    Mar. 3, 2022

Related U.S. Application Data

(63) Continuation-in-part of application No. 15/715,895, filed on Sep. 26, 2017, now Pat. No. 10,668,271.

(60) Provisional application No. 62/776,550, filed on Dec. 7, 2018, provisional application No. 62/756,185, filed on Nov. 6, 2018.

(51) Int. Cl.
    *A61N 1/05*    (2006.01)
(52) U.S. Cl.
    CPC ......... *A61N 1/0539* (2013.01); *A61N 1/0534* (2013.01)
(58) Field of Classification Search
    CPC ............... A61N 1/0539; A61N 1/0534; A61M 2025/02; A61M 2025/024; A61B 2090/103; A61B 90/11
    See application file for complete search history.

(56) References Cited

U.S. PATENT DOCUMENTS

| 5,927,277 | A  | * | 7/1999  | Baudino  | A61N 1/0539 600/386 |
| 6,134,477 | A  | * | 10/2000 | Knuteson | A61N 1/0539 607/115 |
| 2009/0112327 | A1 | * | 4/2009 | Lane | A61N 1/0539 623/17.19 |
| 2013/0197472 | A1 | * | 8/2013 | Skakoon | A61N 1/0539 604/500 |
| 2014/0276418 | A1 | * | 9/2014 | Nelson | A61N 1/0539 604/151 |
| 2019/0091468 | A1 |   | 3/2019 | Buss et al. | |
| 2019/0099596 | A1 | * | 4/2019 | Mirro | A61B 17/7055 |

FOREIGN PATENT DOCUMENTS

EP    1048320 B1    8/2005

OTHER PUBLICATIONS

MEDTRONIC Stimloc Burr Hole Cover and Accessories—924256, Jan. 28, 2020.

* cited by examiner

*Primary Examiner* — Michael W Kahelin
*Assistant Examiner* — Michael A Rizzuto
(74) *Attorney, Agent, or Firm* — Noblitt & Newson, PLLC

(57) ABSTRACT

A lead fixation device for attaching a deep brain stimulation lead within in a burr hole in a human skull. The lead fixation device may comprise a mounting plate having first and second arms. The first arm may comprise a first flange, a first mounting hole, and a first inner wall. The second arm may comprise a second flange, a second mounting hole, and a second inner wall. The first and second arms may comprise first and second arcuate grooves located on the first and second inner walls. When the lead device is in a closed position the first and second arcuate grooves form a guide channel and the first and second inner walls form an exit channel to receive the lead when the lead fixation device is in a closed position.

17 Claims, 11 Drawing Sheets

METHODS AND APPARATUS FOR A LEAD FIXATION DEVICE

CROSS-REFERENCES TO RELATED APPLICATIONS

This application claims the benefit of U.S. Provisional Patent Application No. 62/756,185, filed Nov. 6, 2018, and U.S. Provisional Patent Application No. 62/776,550, filed Dec. 7, 2018 and incorporates the disclosure of each by reference. To the extent that the present disclosure conflicts with any referenced application, however, the present disclosure is to be given priority.

BACKGROUND OF THE TECHNOLOGY

Deep Brain Stimulation (DBS) is an established neurosurgical treatment for multiple conditions including: Parkinson's disease, essential tremor, dystonia, and has been recently approved for medically refractory epilepsy. Responsive neural stimulation also uses implanted electrodes in the brain and is FDA approved. Additional probable indications likely to be approved in the future include: obsessive compulsive disorder, depression and even Alzheimer's disease. The number of permanently implanted brain electrodes continues to increase each year. Each brain electrode requires precise placement and permanent fixation, which allows for years of use. Generally the brain electrodes consist of DBS leads, which are implanted into the brain. The DBS leads are designed for durability and precise control of therapy.

DBS surgery typically involves placement of a single lead through a burr hole or a single twist drill opening, either unilaterally or bilaterally. A burr hole is a relatively small opening made in the bone of the skull to access the intracranial space (the space inside the skull). Burr holes are used to help relieve pressure on the brain when fluid, such as blood, builds up and starts to compress brain tissue. A burr hole is typically made by some form of spinning burr tool which can either be a manual, electric or pneumatic drill. The cutting bit is very much like a drill bit and allows the neurosurgeon to drill through the skull in a controlled fashion. The size of a typical burr hole is 14 mm. The size of a single twist drill opening may range from 2-5 mm in diameter for a single lead position. Other sizes may be contemplated based on the size of the lead fixation device.

In practice a lead is stereotactically implanted through a separate burr hole or single twist drill opening and then secured in place with a lead fixation device. A standard lead fixation device anchors the lead to the skull and covers the burr hole or single twist drill opening drilled through the skull. Standard lead fixation devices are designed for stable and secure fit against the skull and burr hole or single twist drill opening and to protect the lead/clip interface and create a smooth profile over the burr hole or single twist drill opening.

Unfortunately, all currently available lead fixation devices are somewhat cumbersome to use and result in a visible and palpable protrusion under the skin, which is usually bothersome to the patient. The visibility of the current lead fixation devices may also limit the use of DBS leads with bald patients, who may be concerned about the appearance of "horns." One such example is the SureTek™ Burr Hole Cover Kit provided by Boston Scientific®.

SUMMARY OF THE TECHNOLOGY

A lead fixation device for attaching a deep brain stimulation lead within in a burr hole in a human skull. The lead fixation device may comprise a mounting plate having first and second arms. The first arm may comprise a first flange, a first mounting hole, and a first inner wall. The second arm may comprise a second flange, a second mounting hole, and a second inner wall. The first and second arms may comprise first and second arcuate grooves located on the first and second inner walls. When the lead device in a closed position the first and second arcuate grooves form a guide channel and the first and second inner walls form an exit channel to receive the lead when the lead fixation device is in a closed position.

BRIEF DESCRIPTION OF THE DRAWINGS

A more complete understanding of the present technology may be derived by referring to the detailed description when considered in connection with the following illustrative figures. In the following figures, like reference numbers refer to similar elements and steps throughout the figures.

Figure 1:
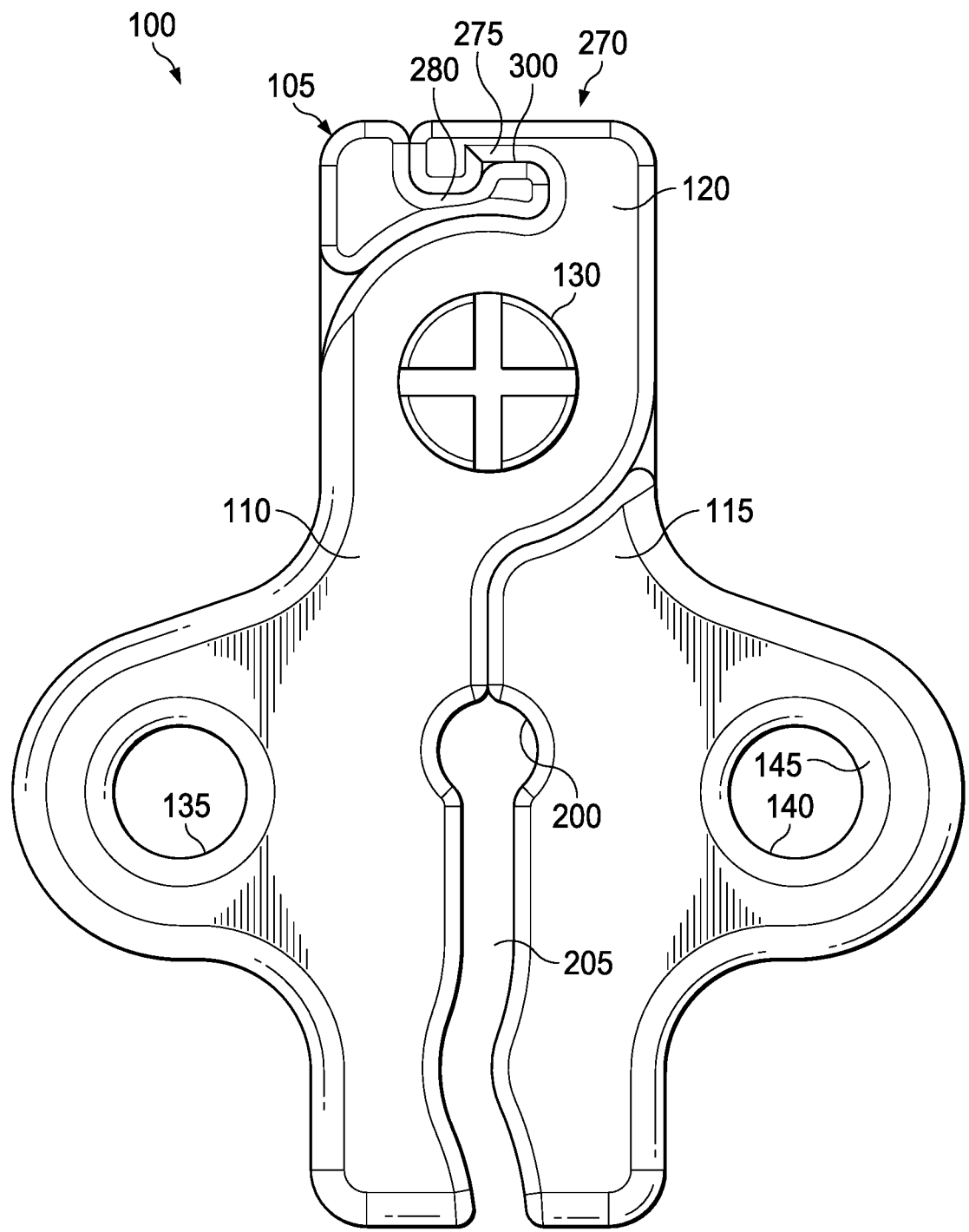
FIG. 1 representatively illustrates a top view of a lead fixation device in a closed position in accordance with various embodiments of the present technology.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may employ various types of materials, connectors, and the like for a lead fixation device, which may carry out a variety of operations suited to a specified application or environment. In addition, the present technology may be practiced in conjunction with any number of systems configured for operation with lead fixation devices, and the systems described are merely exemplary applications for the technology. Further, the present technology may employ any number of conventional techniques for utilizing and practicing lead fixation devices.

Methods and apparatus for providing a lead fixation device designed to minimize an invasive lead placement within the user and reduce visibility of the device to the public. Various representative implementations of the present technology may be applied to any system for minimizing invasive lead placement within the user and reduce visibility of the device to the public. The present technology may be utilized to minimize invasive lead placement within the user and reduce visibility of the device to the public.

The lead fixation devices described below may be comprised of any suitable materials. For example, the lead fixation device may comprise titanium, various plastic materials, or any other suitable medical grade material. In one embodiment, the lead fixation devices may be made of biocompatible Polyether ether ketone ("PEEK") material, which avoids wear and/or excessive compression of the lead. PEEK is a colourless organic thermoplastic polymer in the polyaryletherketone family, typically used in engineering applications. The PEEK material is constructed without sharp edges so that damage to the Deep Brain Stimulation ("DBS") lead does not occur.

Accordingly, a lead fixation device 100 is contemplated that is minimally invasive, smaller, and easier to install than any currently available system. The lead fixation device 100 allows the DBS lead to be placed through a small incision and bone opening than other current lead fixation devices. For example, the present lead fixation device 100 may be implanted in a bone opening of 3 mm. The smaller bone opening may be referred to as a twist drill hole or a biopsy drill hole. It should be understood that the lead fixation device 100 can be sized according to any suitable bone opening. In various embodiments, the lead fixation device 100 may be utilized with a single twist drill opening ranging from 2-5 mm in diameter. The lead fixation device 100 does not require any assembly or removal of the stereotactic at the time of lead fixation. In various embodiments, the height of the lead fixation device 100 may be range approximately 1 mm-3 mm. In one embodiment, the height of the lead fixation device 100 may be approximately 2 mm. In one embodiment, the height of the lead fixation device 100 may be approximately 1 mm. In one embodiment, the height of the lead fixation device 100 may be less than 1 mm.

Figure 2:
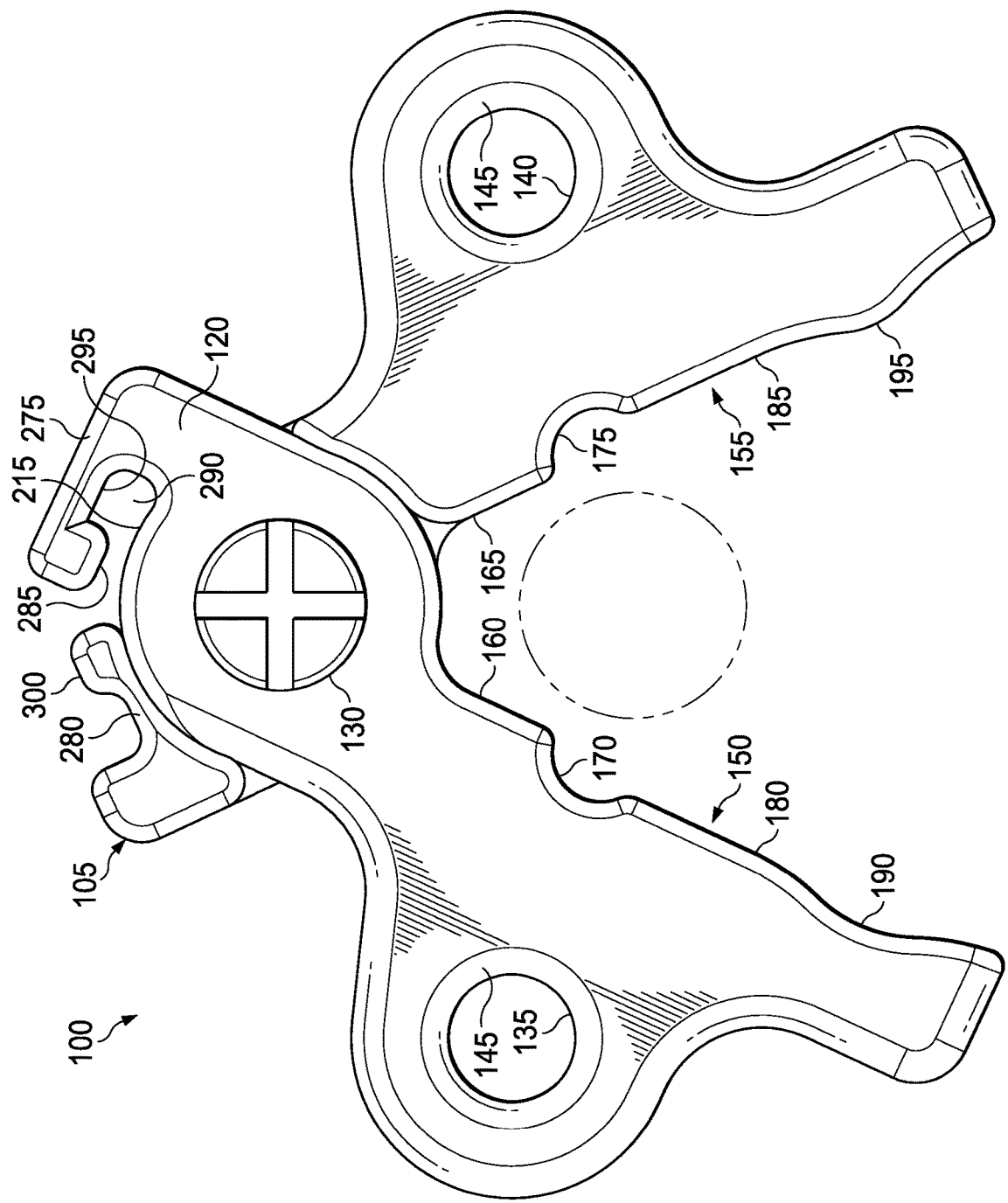
FIG. 2 representatively illustrates a top view of the lead fixation device in an open position in accordance with various embodiments of the present technology.
Figure 3:
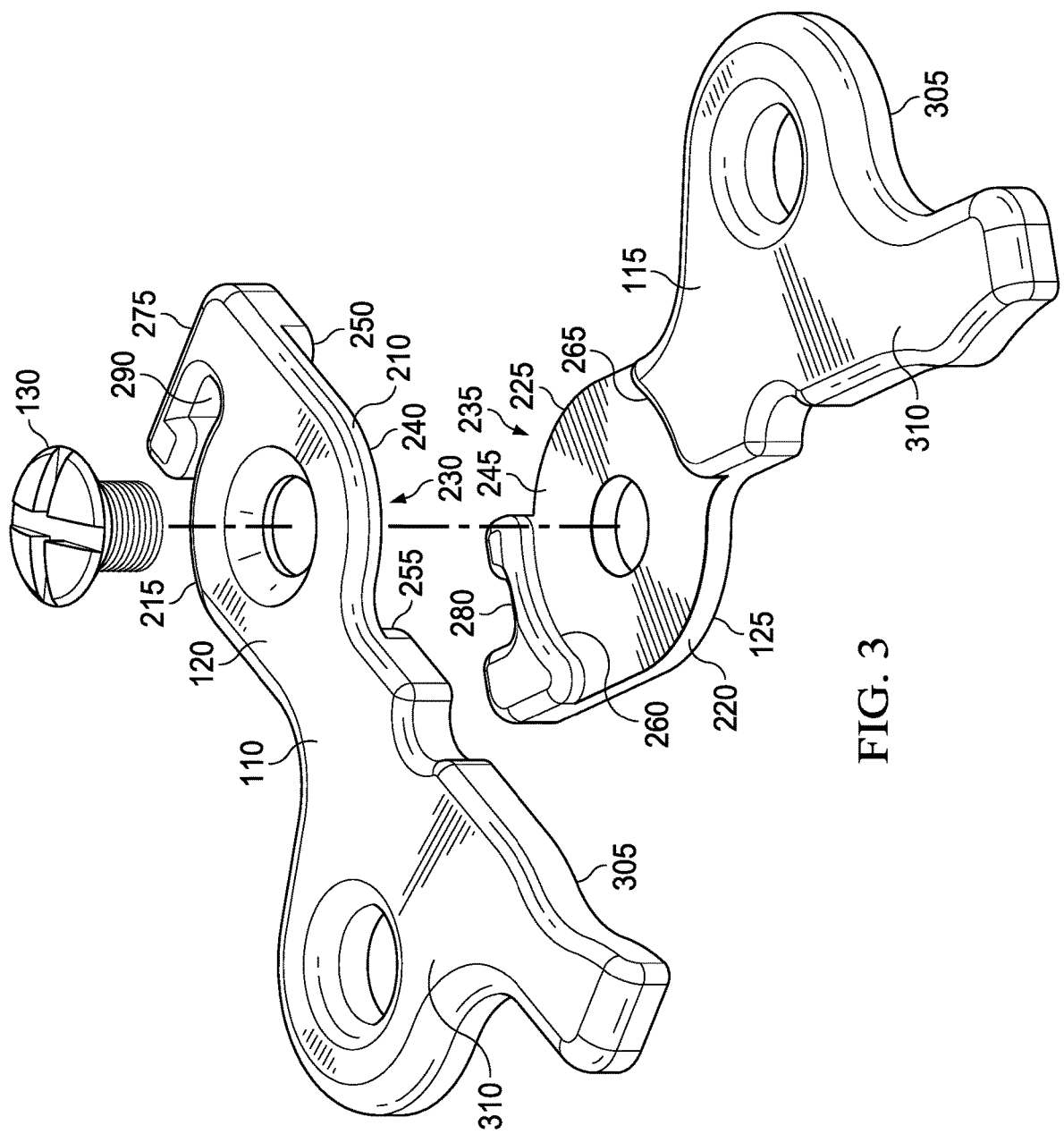
FIG. 3 representatively illustrates an exploded, perspective view of the lead fixation device in an open position in accordance with various embodiments of the present technology FIG. 4 representatively illustrates a top view of an additional embodiment of a lead fixation device in an open position in accordance with various embodiments of the present technology.
Figure 4:
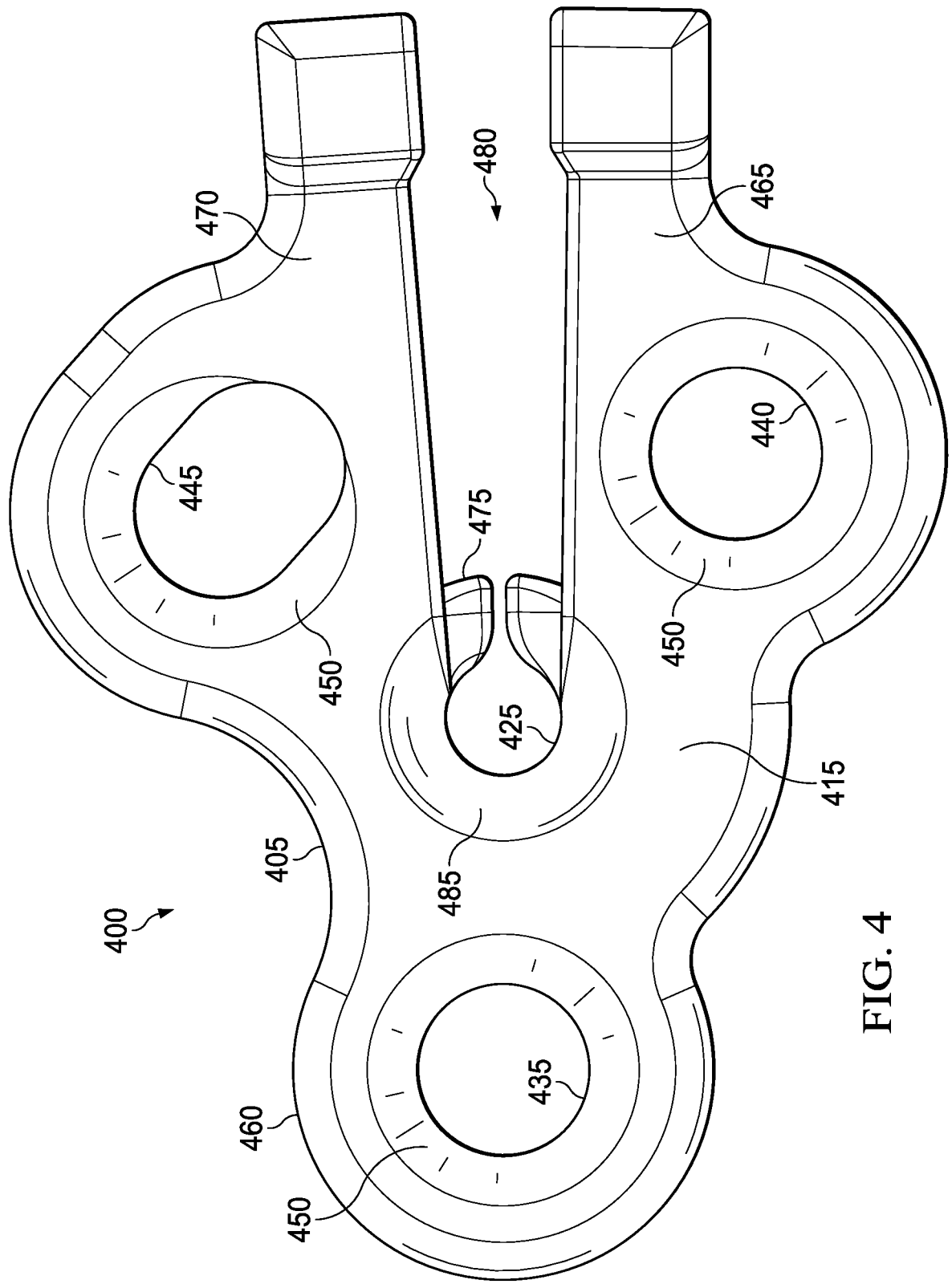
Figure 5:
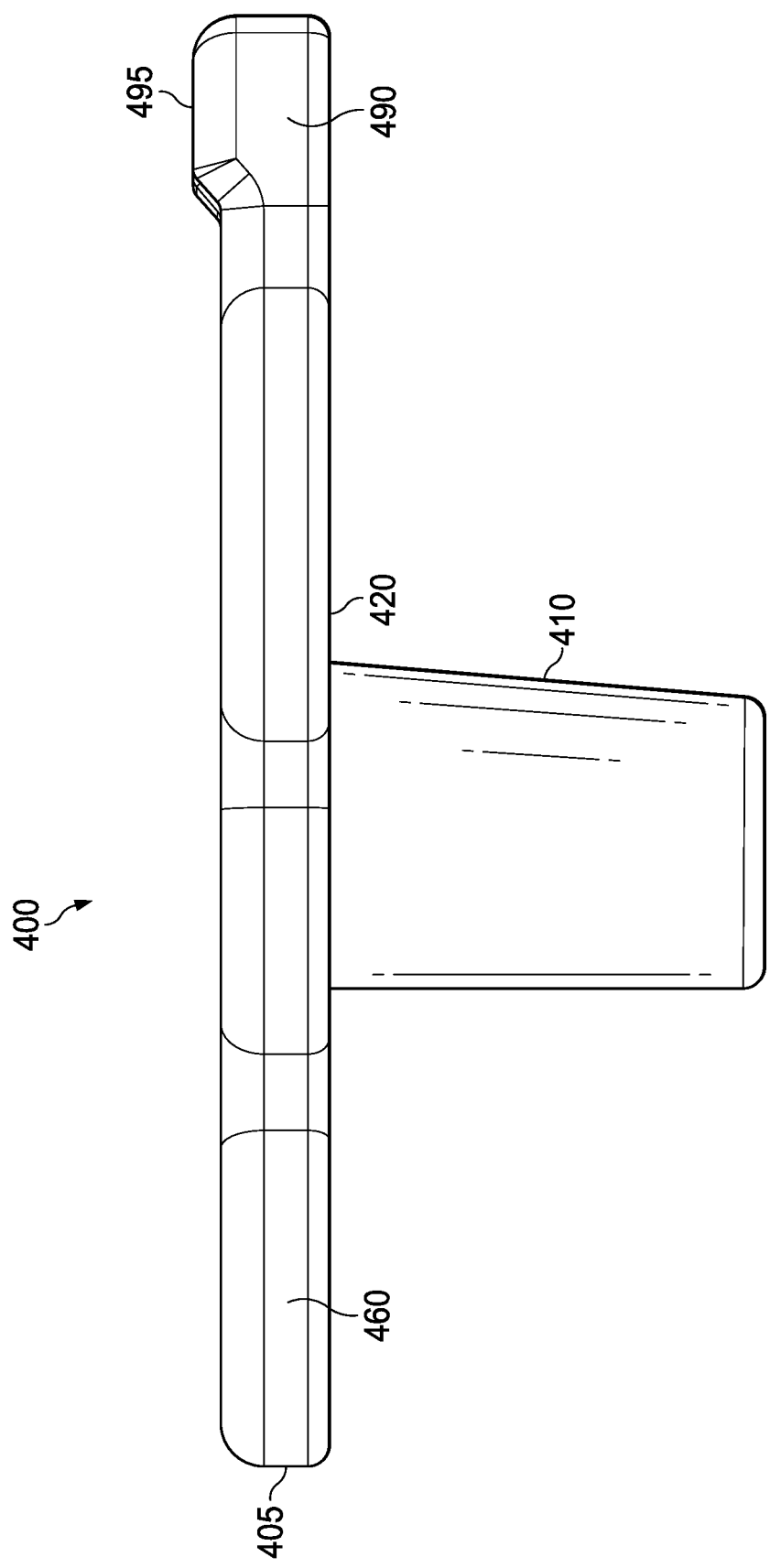
FIG. 5 representatively illustrates a side view of the additional embodiment of a lead fixation device in an open position in accordance with various embodiments of the present technology.
Figure 6:
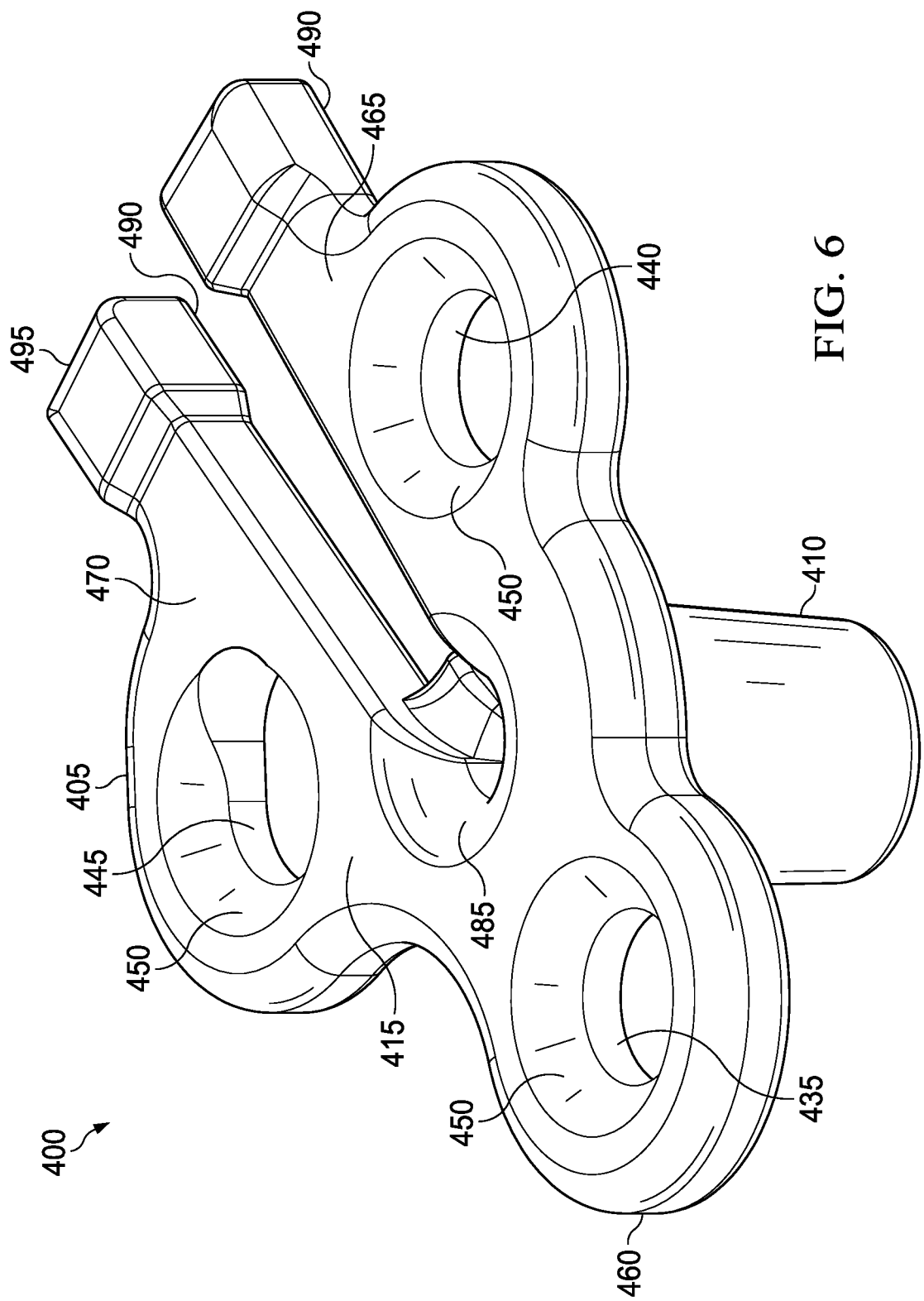
FIG. 6 representatively illustrates a front side, perspective view of the additional embodiment of a lead fixation device in an open position in accordance with various embodiments of the present technology.
Figure 7:
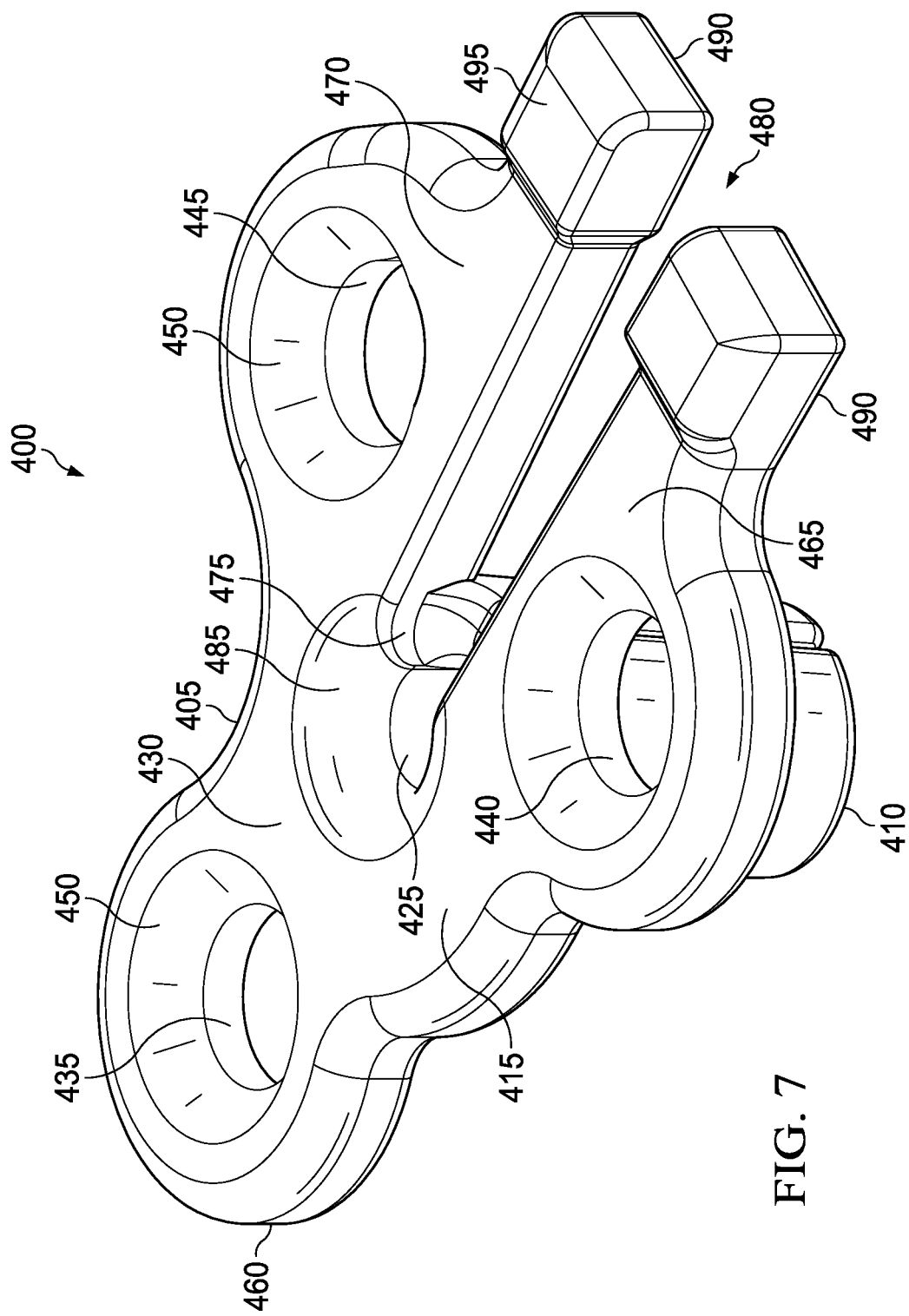
FIG. 7 representatively illustrates a rear side, perspective view of the additional embodiment the lead fixation device in an open position in accordance with various embodiments of the present technology.

In accordance with various embodiments, referring now to FIGS. 1-3, the lead fixation device 100 may comprise a mounting plate 105 comprising a first arm 110 and a second arm 115. In one embodiment, the first and second arms 110, 115 may comprise first and second flanges 120, 125. The first flange 120 of the first arm 110 may be coupled to the second flange 125 of the second arm 115. In one embodiment, first and second flanges 120, 125 of the first and second arms 110, 115 are rotatable and coupled to each other. In one embodiment, first and second flanges 120, 125 of the first and second arms 110, 115 are press-fit together at the rotating hinge site with a circular flange collar. In other words one fitting inside in each arm resides within the other. In another embodiment, a coupling mechanism 130 is used to couple the first and second arms 110, 115 to one another. The coupling mechanism 130 may be any screw, flange or coupling combination that couples the first and second arms 110, 115 to one another. The second arm 115 is rotatable with regard to the first arm 110 such that when the two arms are pressed together, the lead fixation device 100 may secure the DBS lead to the patient/user.

In various embodiments, the first and second arms 110, 115 of the mounting plate 105 may comprise a pair of mounting holes 135, 140, which extend therethrough. The first and second mounting holes 135, 140 may be generally cylindrical. The first and second mounting holes 135, 140 may be fixed once installed. Each of the first and second mounting holes 135, 140 may contain an inwardly beveled sidewall 145 that receives a countersunk head of a mounting screw (not shown). Each of the first and second mounting holes 135, 140 may be located at approximately the midpoint of the first and second arms 110, 115.

In one embodiment, the first and second arms 110, 115 of the mounting plate 105 may each comprise an inner wall 150, 155. The inner walls 150, 155 each may comprise a mating portion 160, 165, an arcuate groove 170, 175, and a longitudinal wall 180, 185. In one embodiment, the longitudinal walls 180, 185, may comprise a curved portion 190, 195.

FIG. 1 shows the lead fixation device 100 in closed position while FIGS. 2 and 3 show the lead fixation device 100 in an open position. In the closed position, mating portion 160, 165 abut and the arcuate groove 170, 175 form at least one guide channel 200 and the longitudinal walls 180, 185 form an exit channel 205. The guide channel 200 receives the DBS lead that exits the user's skull. In the closed position, the exit channel 205 formed within the space between the first and second arms 110, 115 guides the DBS lead that exits the user's skull in a desired direction. In one embodiment, the first and second mounting holes 135, 140 are located generally outwardly from the at least one guide channel 200. The curved portions 190, 195 and the longitudinal walls 180, 185 when combined in the closed position form a "slalom slot" for press fitting the lead in its final position, after the lead stylet is removed, and to secure the lead against any delayed migration or external damage at the bending point where the lead exits the skull via the guide channel 200.

Referring now to FIG. 3, the first and second flanges 120, 125 will be discussed. In various embodiments, the first flange 120 may comprise first and second outer walls 210, 215 and the second flange may comprise first and second outer walls 220, 225. The outer walls 210, 215, 220, and 225 are generally curved and assist in the coupling and rotation of the first and second flanges 120, 125. In various embodiments, the first and second flanges 120, 125 may comprise first and second mating portions 230, 235. In various embodiments, each of the first and second mating portions may comprise recessed areas 240, 245 where a portion of the first and second flanges 120, 125 has been removed. In various embodiments, the first flange 120 may comprise first and second collar walls 250, 255 and the second flange 125 may comprise first and second collar walls 260, 265. The first and second collar walls 250, 255 of the first flange 120 are oriented opposite one another with the recessed area 240 locate there between. The first and second outer walls 210, 215 are located on the perimeter of the recessed area 240 between the first and second collar walls 250, 255. The first and second collar walls 260, 265 of the second flange 125 are oriented opposite one another with the recessed area 245 locate there between. The first and second outer walls 220, 225 are located on the perimeter of the recessed area 245 between the first and second collar walls 260, 265.

When assembled the recessed areas 240, 245 of the first and second mating portions 230, 235 contact one another; the outer walls 210, 215 of the first flange 120 are located adjacent the first and second collar walls 260, 265 of the second flange 125; and the outer walls 220, 225 of the second flange 125 are located adjacent the first and second collar walls 250, 255 of the first flange 120. This configuration allows the first arm 110 and second arm 115 to rotate with respect to each other and the height of the lead fixation device 100 to remain consistent.

In various embodiments, the lead fixation device 100 may comprise a locking mechanism 270. The locking mechanism 270 may comprise first and second fingers 275, 280. The first finger 275 depends from an upper surface of the first flange 120 of the first arm 110 and comprises a raised portion 285. The first finger 275 is oriented such that a space 290 is formed between a lower surface 295 of the first finger 275 and the outer wall 215. The second finger 280 depends from an upper surface of the second flange 125 of the second arm 115 and comprises a raised portion 300. When the lead fixation device 100 is oriented in the closed position of FIG. 1, the raised portion 300 is received within the space 290 and the raised portions 285, 300 lock the first and second arms 110, 115 of the lead fixation device 100.

A lower surface 305 of the mounting plate 105 generally abuts the patient/user's skull while an upper surface 310 of the mounting plate 105 is generally flush with or sits on top of the patient/user's scalp. The lower surface 305 of the mounting plate 105 may be generally flat so that the lead fixation device is generally flush with the patient/user's scalp. This configuration provides a generally invisible or inconspicuous lead fixation device.

In operation, the DBS lead is inserted within a burr hole or a single twist drill opening in the user/patient's skull. While the lead fixation device 100 in oriented in the open position, shown in FIG. 2, the DBS lead is placed within the guide channel 200. The doctor may then press or pinch the arms 115, 120 toward one another and insert screws within the pair of mounting holes 135, 140 to fasten the lead fixation device 100 to the skull. The DBS lead is then placed within the exit channel 205 formed within the space between the first and second arms 110, 115.

In accordance with various embodiments, referring now to FIGS. 4-8, the lead fixation device 400 comprises a mounting plate 405 and an insertion collar 410. The insertion collar 410 may be located at a central portion 415 of the mounting plate 405. The insertion collar 410 depends downwardly from a lower surface 420 of the mounting plate 405. The insertion collar 410 may be generally cylindrical and comprise an insertion hole 425 where a DBS lead 430 may be placed. In one embodiment, the insertion collar 410 may taper inwardly as it depends away from the lower surface 420. The insertion hole 425 may extend though to an upper surface of the mounting plate 405.

The mounting plate 405 may comprise a pair of mounting holes 435, 440 and a compression hole 445, which extend therethrough. The first and second mounting holes 435, 440 may be generally cylindrical. The first and second mounting holes 435, 440 may be fixed once installed. Each of the first and second mounting holes 435, 440 contains an inwardly beveled sidewall 450 that receives a countersunk head of a mounting screw 455. The compression hole 445 may comprise an elongate hole that allows for adjustment of the lead fixation device 400 during installation.

The first mounting hole 435 may be located on a flange 460 that extends from the central portion 415 of the mounting plate 405. The second mounting hole 440 and the compression hole 445 reside on a pair of arms 465, 470 that extend from the central portion 415 opposite of the first mounting hole 435. A space exists between the arms 465, 470 such that they can be pressed inwardly toward one another during installation. The arm 470 containing the compression hole 445 is rotatable with regard to the arm 465 containing the second mounting hole 440 such that when the two arms 465, 470 are pressed together, the space between the two arms 465, 470 creates a channel 480 to guide the DBS lead 430 exiting the patient/user.

The insertion hole 425 may comprise a cutout area 475 where a portion of a sidewall 485 of the insertion hole 425 is removed. The location of the cutout area 475 between the arms 465, 470 allows the arm 470 containing the compression hole 445 to move with regard to the arm 465 containing the second mounting hole 440. The arms 465, 470 each contain a finger flange 490 with a raised portion 495. The raised portions 495 allow the physician to press or pinch the arms 465, 470 toward one another during installation.

The lower surface 420 of the mounting plate 405 generally abuts the patient/user's skull and the insertion collar 410 may be may be inserted into the bone opening, burr hole or single twist drill opening of patient/user. The upper surface of the mounting plate 405 is generally flush with or sits on top of the patient/user's scalp. This configuration provides a generally invisible or inconspicuous lead fixation device.

Figure 8:
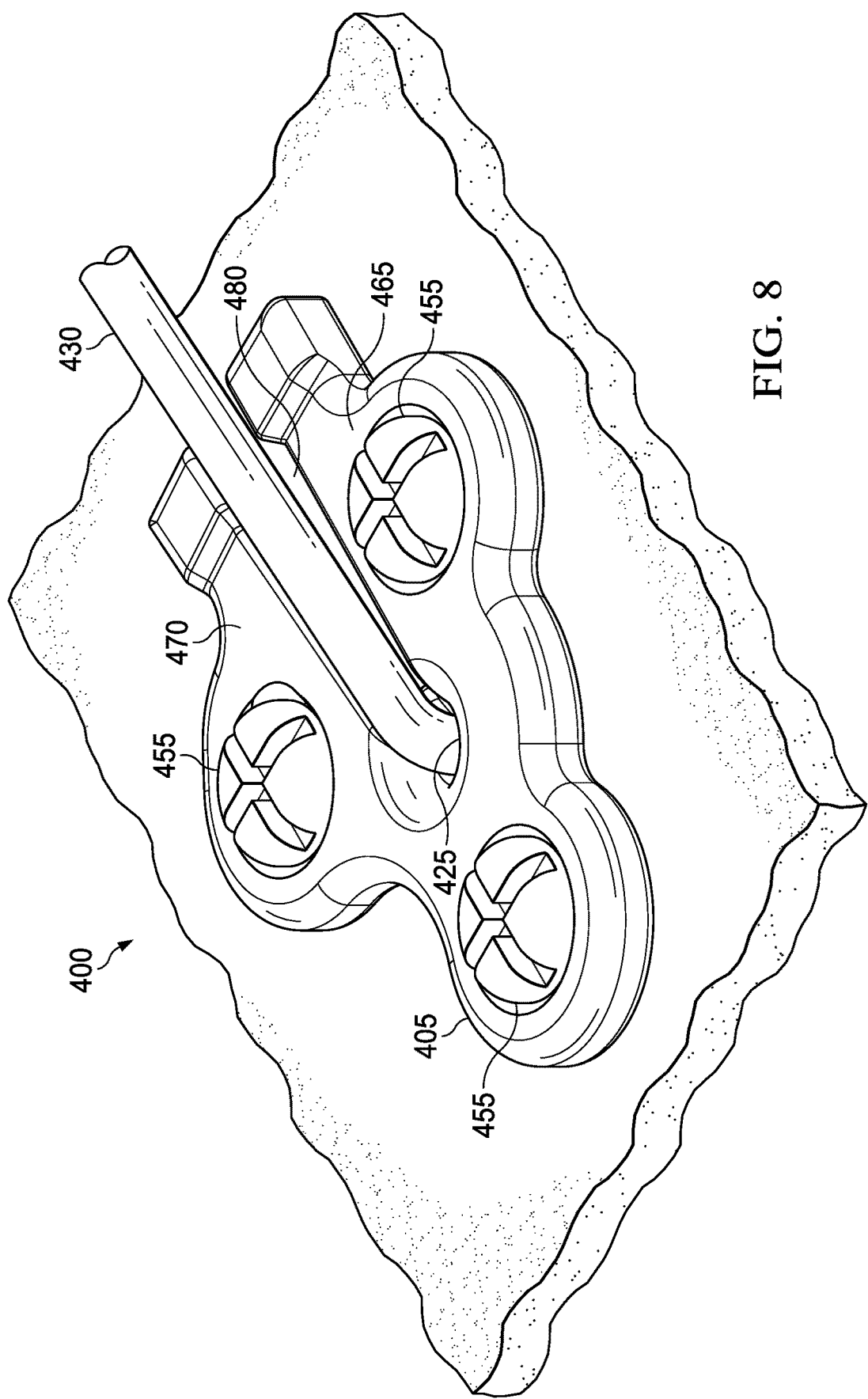
FIG. 8 representatively illustrates a front side, perspective view the additional embodiment of the lead fixation device in an installed position in accordance with various embodiments of the present technology.

FIGS. 4-7 show the lead fixation device 400 in an open position while FIG. 8 shows the lead fixation device 400 in an installed, closed position. In the closed position, the channel 480 formed within the space by the arms 465, 470 guides the DBS lead 430 that exits the user's skull in a desired direction.

In operation, the DBS lead 430 is inserted within a burr hole or single twist drill opening in the user/patient's skull. While the lead fixation device 400 in oriented in the open position, shown in FIGS. 4-7, the DBS lead 430 is placed within the insertion hole 425 located in the insertion collar 410. The doctor may then fasten the lead fixation device 400 to the skull by inserting screws 455 within the first and second mounting holes 435, 440. The DBS lead is then placed between the arms 465, 470. The doctor may then press or pinch the raised portions 495 of the arms 465, 450 toward one another and insert a screw 455 within the compression hole 445. The DBS lead 430 will now reside within the channel 480 formed within the space between the arms 465, 470.

Figure 9:
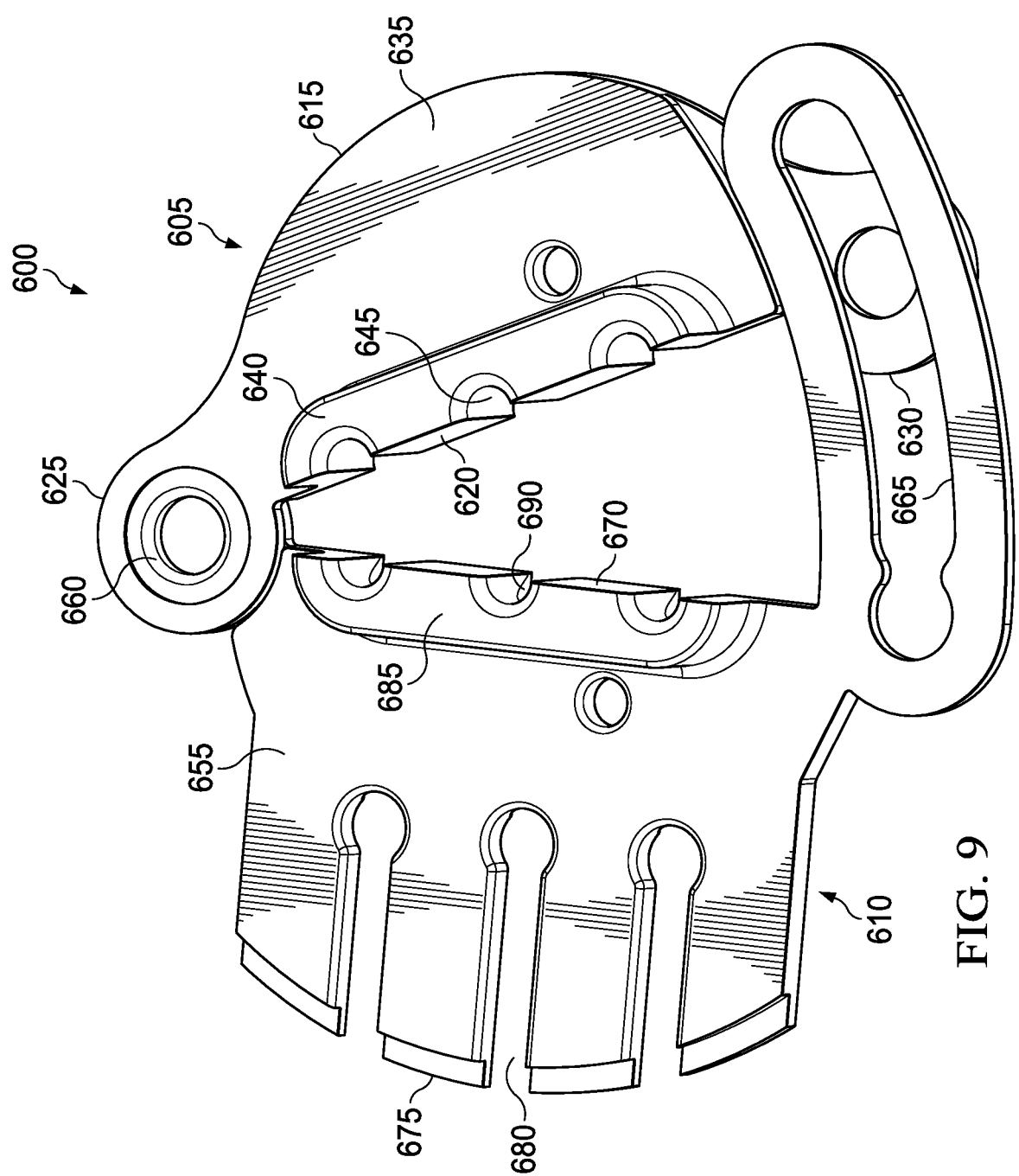
FIG. 9 representatively illustrates a bottom view of an additional embodiment of a lead fixation device in an open position in accordance with various embodiments of the present technology.
Figure 10:
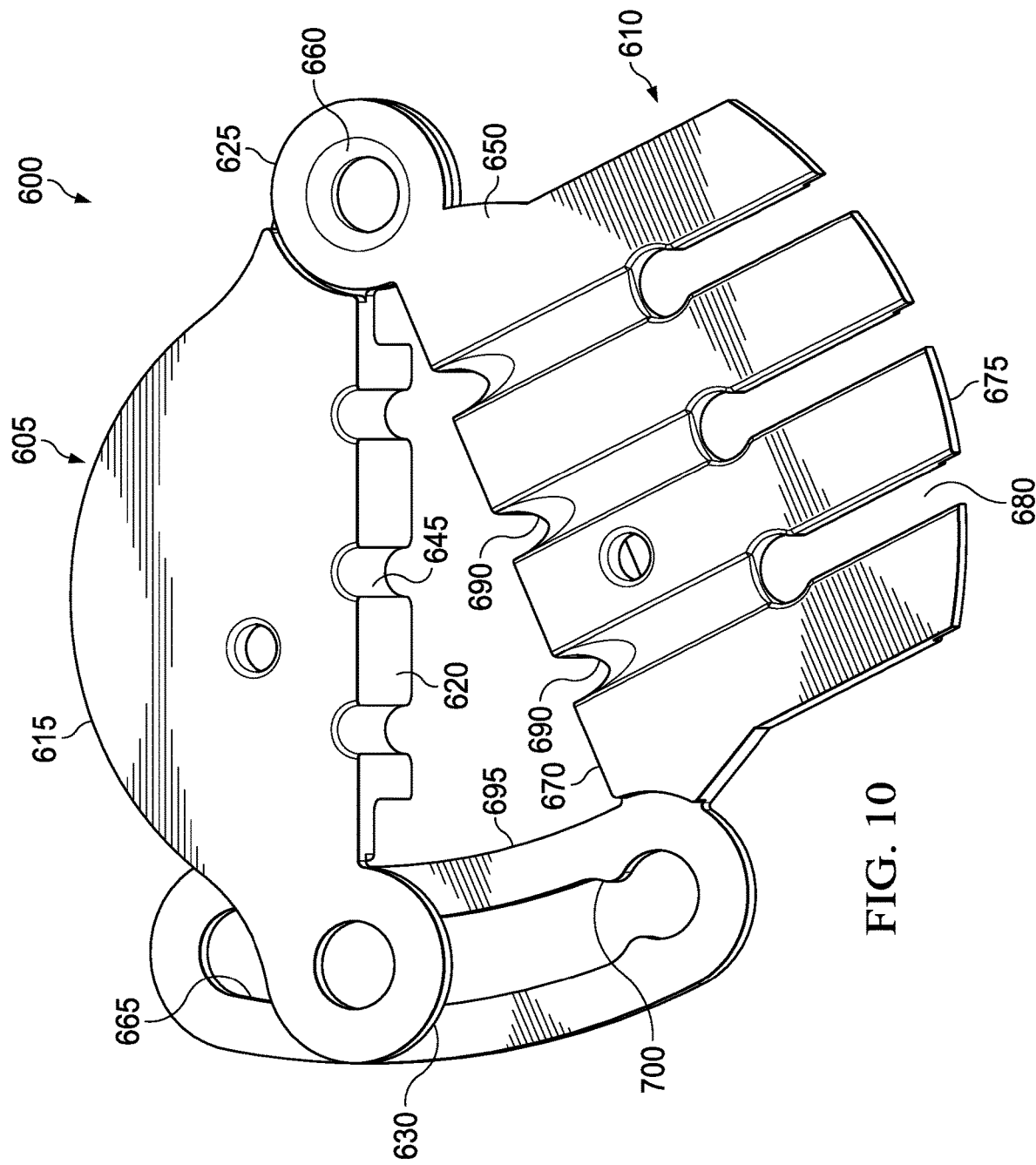
FIG. 10 representatively illustrates a top view of the additional embodiment of the lead fixation device in an open position in accordance with various embodiments of the present technology.
Figure 11:
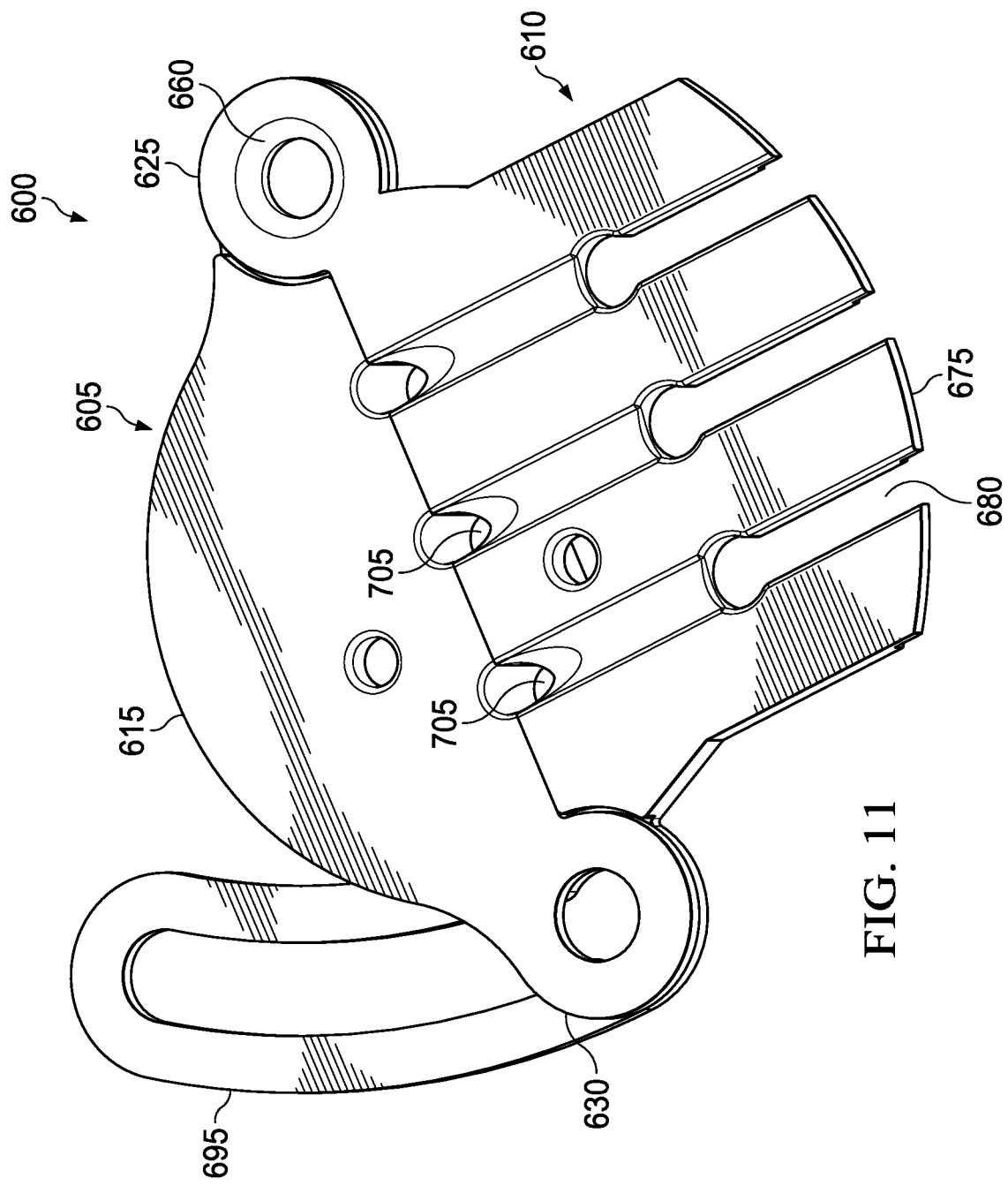
FIG. 11 representatively illustrates a top view of the additional embodiment of the lead fixation device in a closed position in accordance with various embodiments of the present technology.

Referring now to FIGS. 9-11, in another embodiment, a low profile lead fixation device 600 is contemplated that is both faster and easier to use than any currently available system. The low profile lead fixation device 600 does not require any assembly or removal of the stereotactic at time of lead fixation. The low profile lead fixation device 600 may be on the order of a millimeter in thickness, produces no visible bump, and avoids the need for countersinking the fixation device by excessive skull drilling at the time of lead placement. In various embodiments low profile lead fixation device 600 may range from approximately 2 mm to 0.5 mm in thickness. In one embodiment, low profile lead fixation device 600 may be 1 mm in thickness. In one embodiment, low profile lead fixation device 600 may be less than 1 mm in thickness.

In accordance with various embodiments, referring now to FIGS. 9-11, the low profile lead fixation device 600 will be discussed. The low profile lead fixation device 600 comprises a mounting plate having a first arm 605 and a second arm 610. The first and second arms 605, 610 are rotatable and coupled to each other. In one embodiment the first and second arms 605, 610 are press-fit together at a rotating hinge site with a circular flange collar. In other words, one fitting inside in each arm resides within the other. The second arm 610 is rotatable with regard to the first arm 605 such that when the two arms are pressed together, the lead fixation device 600 may secure the DBS lead to the patient/user.

The first arm 605 may comprise a curved edge 615 and a substantially straight edge 620 located between a first flange 625 and a second flange 630. A lower surface 635 of the first arm 605 may comprise a raised protrusion 640 residing along the substantially straight edge 620. The raised protrusion 640 may comprise at least one arcuate groove 645. In one embodiment the raised protrusion 640 may comprise 3 arcuate grooves 645.

The second arm 610 may comprise an upper surface 650, a lower surface 655, a first flange 660, and a ring slot 665. The second arm 610 may comprise a substantially straight edge 670 and a curved edge 675 that reside between the first flange 660 and the ring slot 665. The second arm 610 may comprise at least one exit channel 680. In one embodiment, the second arm 610 may comprise 3 exit channels 680. In one embodiment, each of the exit channels 680 may comprise a semi-circular hole. The semi-circular holes at each exit channel 680 are provided to allow easy insertion of the DBS lead wire for subsequent press fitting into the exit channel 680 for a secondary friction based fixation. The exit channels 680 are oriented generally perpendicular to the substantially straight edge 670 and extend from the straight edge 670 towards the curved edge 675.

The lower surface 655 of the second arm 610 may comprise a raised protrusion 685 residing along the substantially straight edge 670. The raised protrusion 685 may comprise at least one arcuate groove 690. In one embodiment, the raised protrusion 685 may comprise 3 arcuate grooves 690.

The lower surfaces 635, 655 of the first and second arms 610, 615 generally abut the patient/user's skull while the upper surface 650 is flush with patient/user's scalp. This configuration provides a generally invisible or inconspicuous lead fixation device.

The first flange 625 of the first arm 605 is coupled to the first flange 660 of the second arm 610. The two arms 605, 610 may be press fit together at the circular rotating hinge located at the first flanges 625, 660. The coupling of the first flanges 625, 660 causes the second arm 610 to rotate with respect to the first arm 605. The second flange 630 of the first arm 605 is aligned with the ring slot 665. An inner wall 695 of the ring slot 665 abuts the curved edge 615 of the first arm 605 and slides along when the second arm 610 is rotated about the first arm 605. The ring slot 665 may comprise a pair of notches 700, which are designed to engage the screw when the lead fixation device 600 is attached to the user.

FIGS. 9 and 10 show the lead fixation device 600 in an open position while FIG. 11 shows the lead fixation device 600 in a closed position. In the closed position, the raised protrusions 640, 685 abut and the arcuate grooves 645, 690 form at least one guide channel 705. In one embodiment 3 guide channels 705 are formed. The guide channels 705 receive the DBS lead that exits the user's skill.

In operation, the DBS lead is inserted within a burr hole in the user/patient's skull. While the lead fixation device 600 in oriented in the open position, shown in FIGS. 9 and 10, the DBS lead is placed within the arcuate groove 645 located in the raised protrusion 640 of the first arm 605. The second arm 610 is then rotated to the closed position, shown in FIG. 3, where the arcuate groove 690 located in the raised protrusion 685 of the second arm 610 forms the guide channel 705 and clamps the DBS lead to hold it in place. A stylet within the DBS lead may then be removed and the DBS lead may be pressed to fold over and fit within the exit channel 680 for a second point of fixation for added security. The doctor may then fasten the lead fixation device 600 to the skull by inserting screws within the first flanged connection 625, 660 and the second flange 630 and ring slot 665 connection, These and other embodiments for methods and apparatus for a lead fixation device may incorporate concepts, embodiments, and configurations as described above. The particular implementations shown and described are illustrative of the technology and its best mode and are not intended to otherwise limit the scope of the present technology in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

The technology has been described with reference to specific exemplary embodiments. Various modifications and changes, however, may be made without departing from the scope of the present technology. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present technology and are accordingly not limited to the specific configuration recited in the specific examples. Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to an exemplary embodiment. However, changes and modifications may be made to the exemplary embodiment without departing from the scope of the present technology. These and other changes or modifications are intended to be included within the scope of the present technology, as expressed in the following claims.

The invention claimed is:

1. A lead fixation device for attaching a deep brain stimulation lead within in a burr hole in a human skull, the lead fixation device being movable from an open position to a closed position, comprising:
   a mounting plate comprising:
      a first arm comprising:
         a first flange,
         a first mounting hole, and
         a first inner wall;
      a second arm comprising:
         a second flange connected to the first flange at a connection point,
         a second mounting hole, and
         a second inner wall;
      wherein the first arm is rotatably coupled to the second arm at the connection point between the first flange and the second flange, and wherein the first mounting hole and the second mounting hole do not overlap with any mounting hole when the lead fixation device is in the closed position.

2. The lead fixation device of claim 1, comprising:
a first arcuate groove located on the first inner wall of the first arm, and
a second arcuate groove located on the second inner wall of the second arm.

3. The lead fixation device of claim 2, wherein the first and second arcuate grooves form a guide channel to receive the lead when the lead fixation device is in a closed position.

4. The lead fixation device of claim 3, wherein the first and second mounting holes are located outwardly of the guide channel.

5. The lead fixation device of claim 1, wherein the first and second inner walls form an exit channel to receive the lead when the lead fixation device is in a closed position.

6. The lead fixation device of claim 1, wherein the first flange is rotatably coupled to the second flange.

7. The lead fixation device of claim 1, wherein:
the first mounting hole is located at approximately a midpoint between an upper end and a lower end of the first arm, and
the second mounting hole is located at approximately a midpoint between an upper end and a lower end of the second arm.

8. The lead fixation device of claim 1, further comprising a locking mechanism comprising:
a first finger having a raised portion and depending from an upper surface of the first flange, and
a second finger having a raised portion depending from an upper surface of the second flange;
wherein the first and second raised portions are configured to lock the lead fixation device in a closed position.

9. The lead fixation device of claim 1, wherein each of the first and second inner walls comprise a curved portion, which are oriented parallel to one another.

10. A lead fixation device for attaching a deep brain stimulation lead within in a burr hole in a human skull, the lead fixation device being movable from an open position to a closed position, comprising:
   a mounting plate comprising:
      a first arm comprising:
         a first flange,
         a first mounting hole,
         a first inner wall, and
         a first arcuate groove located on the first inner wall of the first arm;
      a second arm comprising:
         a second flange connected to the first flange at a connection point,
         a second mounting hole,
         a second inner wall, and
         a second arcuate groove located on the second inner wall of the second arm;
      wherein the first arm is rotatably coupled to the second arm at the connection point between the first flange and the second flange, wherein the first and second arcuate grooves form a guide channel and the first and second inner walls form an exit channel to receive the lead when the lead fixation device is in a closed position, and wherein the first mounting hole and the second mounting hole do not overlap with any mounting hole when the lead fixation device is in the closed position.

11. The lead fixation device of claim 10, wherein the first flange is rotatably coupled to the second flange.

12. The lead fixation device of claim 10, wherein:
the first mounting hole is located at approximately a midpoint between an upper end and a lower end of the first arm, and
the second mounting hole is located at approximately a midpoint between an upper end and a lower end of the second arm.

13. The lead fixation device of claim 10, wherein the first and second mounting holes are located outwardly of the guide channel.

14. A method of attaching the lead fixation device of claim 10 to a deep brain stimulation lead exiting a burr hole implanted in a human skull, comprising:
placing the lead within the first and second arcuate grooves;
pressing the first and second arms toward each other to form the guide channel and exit channel;
inserting screws within the first and second mounting holes to fasten the lead fixation device to the human skull;
placing the lead within the exit channel.

15. A lead fixation device for attaching a deep brain stimulation lead within in a burr hole in a human skull, comprising:
   a mounting plate comprising:
      a first arm comprising:
         a first flange,
         a first mounting hole,
         a first inner wall, and
         a first arcuate groove located on the first inner wall of the first arm;

a second arm comprising:
- a second flange connected to the first flange at a connection point,
- a second mounting hole,
- a second inner wall, and
- a second arcuate groove located on the second inner wall of the second arm;

wherein the first arm is rotatably coupled to the second arm at the connection point between the first flange and the second flange, wherein the first and second arcuate grooves form a guide channel and the first and second inner walls form an exit channel to receive the lead when the lead fixation device is in a closed position, and wherein the first mounting hole and the second mounting hole do not overlap with any mounting hole when the lead fixation device is in the closed position.

16. The lead fixation device of claim 15, wherein:
the first mounting hole is located at approximately a midpoint between an upper end adjacent to the connection point and a lower end opposite of the connection point of the first arm, and
the second mounting hole is located at approximately a midpoint between an upper end adjacent to the connection point and a lower end opposite of the connection point of the second arm.

17. The lead fixation device of claim 16, wherein the first and second mounting holes are located outwardly of the guide channel.

\* \* \* \* \*